United States Patent
Frank et al.

(10) Patent No.: US 7,935,798 B2
(45) Date of Patent: May 3, 2011

(54) METHOD FOR THE EXTRACTION OF INTRACELLULAR PROTEINS FROM A FERMENTATION BROTH

(75) Inventors: Timothy C. Frank, Midland, MI (US); Felipe A. Donate, Midland, MI (US); Jefry E. Shields, San Diego, CA (US); Kai Li, Lafayette Hill, PA (US); Jeffrey R. Allen, Poway, CA (US)

(73) Assignee: Dow Global Technologies LLC, Midland, MI (US)

( * ) Notice: Subject to any disclaimer, the term of this patent is extended or adjusted under 35 U.S.C. 154(b) by 1065 days.

(21) Appl. No.: 10/590,185

(22) PCT Filed: Feb. 18, 2005

(86) PCT No.: PCT/US2005/005309
§ 371 (c)(1),
(2), (4) Date: Apr. 2, 2007

(87) PCT Pub. No.: WO2005/087791
PCT Pub. Date: Sep. 22, 2005

(65) Prior Publication Data
US 2009/0023902 A1 Jan. 22, 2009

Related U.S. Application Data

(60) Provisional application No. 60/548,403, filed on Feb. 27, 2004.

(51) Int. Cl.
*C07K 1/14* (2006.01)
(52) U.S. Cl. ......... 530/412; 530/418; 530/421; 530/422
(58) Field of Classification Search .................. None
See application file for complete search history.

(56) References Cited

U.S. PATENT DOCUMENTS

| | | | | |
|---|---|---|---|---|
| 4,011,137 A | * | 3/1977 | Thompson et al. | 435/96 |
| 5,304,310 A | * | 4/1994 | Lang et al. | 210/639 |
| 5,628,906 A | | 5/1997 | Shinnar et al. | |
| 2003/0003534 A1 | | 1/2003 | Sheppard | |

FOREIGN PATENT DOCUMENTS

| | | |
|---|---|---|
| GB | 2 333 526 A | 9/1998 |
| WO | WO 00/12537 | 3/2000 |

OTHER PUBLICATIONS

Blanch, Harvy W., et al., "Biochemical Engineering", Marcel Dekker, Inc., New York, NY. 1997. ISBN: 0-8247-0099-6.
International Search Report PCT/US2005/005309.
Johansson, Hans-Olaf et al., "Thermoseparating Water/Polymer System: A novel One-Polymer Aqueous Two-Phase System for Protein Purification", Biotechnology and Bioengineering, vol. 66, No. 4, 1999, pp. 247-257.
Krei, Georg et al., "Extraction of α-amylase using BDBAC-reversed micelles", Bioseparation 4: 175-183, 1995 XP008047247, the Netherlands.
Lotwin, Jorge, "Oxidative Renaturation of Hen Egg-White Lysozyme in Polyethylene Glycol-Salt Aqueous Two-Phase Systems", Biotechnology and Bioengineering, vol. 65, No. 4, Nov. 20, 1999, pp. 437-446.
Louwrier, Ariel, "Model isolations of nucleic acids from prokaryotic and eukaryotic sources using an organic/aqueous biphasic system" Biotechnology Techniques, I3: 329-330, 1999, Klower Academic Publishers. Netherlands.
Louwrier, Ariel, "Model phase separations of proteins using aqueous/ethanol components", Biotechnology Techniques. vol. 12, No. 5, 1998.
Louwrier, Ariel, "Nucleic Acid Removal from *Taq* Polymerase Preparation Using an Aqueous/Organic Biphasic System" BioTechniques vol. 27:444-445 No. 3, Sep. 1999.
Sivars, Ulf, "Mechanisms of phase behavior and protein partitioning in detergent/polymer aqueous two-phase systems for purification of integral membrane proteins[1]", Biochemica et Biophysica Acta 1474 (2000) 133-146.
Sivars, Ulf, "Protein Partitioning in weakly charged polymer-surfactant aqueous two-phase systems", Journal of Chromatography B. 680 (1996) 43-53.

* cited by examiner

*Primary Examiner* — Anish Gupta
(74) *Attorney, Agent, or Firm* — Jarett K. Abramson

(57) ABSTRACT

A method for extracting an intracellular peptide, protein or other polypeptide from a whole fermentation broth using a water miscible alcohol, or a water miscible or partially water miscible glycol ether.

13 Claims, No Drawings

METHOD FOR THE EXTRACTION OF INTRACELLULAR PROTEINS FROM A FERMENTATION BROTH

This application claims the benefit of U.S. Provisional Patent Application Ser. No. 60/548,403, filed Feb. 27, 2004.

The present invention relates to a process for the extraction of intracellular proteins including enzymes and therapeutic proteins from fermentation broth using an organic solvent.

Enzymes are highly efficient protein catalysts which are involved in almost every biological reaction. The enzymes are grouped in into six major classes on the basis of the type of reaction catalyzed; that is, Oxidoreductase, Transferase, Hydrolase, Lyase, Isomerase and Ligase. Enzymes find use in chemical analysis, clinical diagnosis and a broad range of industrial applications. Enzymes may be extracted from any living organism but most are obtained by the fermentation of micro-organisms. Industrial preparation of industrial enzymes aims for economy, effectiveness and safety.

Therapeutic proteins are proteins with specific biological activity that make them effective as pharmaceutical agents or drugs for treatment of disease, or as adjuncts to therapy used in combination with a drug or mixture of drugs. In certain cases, therapeutic proteins may be produced via bacterial fermentation using the methods of genetic engineering to cause the host microbe to produce a specific protein or mixture of proteins having the desired activity. Often, these recombinant proteins are produced within the cell of the organism and must be recovered from the cell after harvesting the broth. Because therapeutic proteins are used as drugs or in combination with drugs, the purity of the isolated protein or protein mixture is a critical factor in their manufacture. This is especially important for proteins that must be injected into the bloodstream to effectively treat disease.

Methods used to recover proteins from fermentation broths can essentially be categorized in two basic methods:

(i) when the host cells are able to secrete proteins outside the cells into a growth medium (extracellular proteins), the media in which the cells grow is collected and the proteins are harvested from the liquid phase, sometimes as the cells continue to grow. This is desirable as it provides the protein in a medium that is not loaded with other cellular components like DNA, host cell proteins, etc. This is typically done in mammalian cell systems but there have been recent advances in prokaryotic cell systems like *E. coli*. The recovery of the desired protein from the media in which the cell grows involves filtration, chromatography, etc. and more commonly in bacterial cell lines like *E. coli* and *P. fluorescens*, the protein is produced and sequestered inside the cell (intracellular protein). In order to recover the intracellular protein it is necessary first to get it out of the cell. Cellular disruption techniques like microfluidization, osmotic shock, heating, pH adjustment work well often but the difficulty in isolating the desired protein from the rest of the cellular components becomes a challenge as once the cell's integrity is disrupted all of the cell's proteins, DNA and other biomolecules, are spilled into the solution that contains the targeted protein. Additionally, when bacterial cells over express a protein/enzyme, the vast amounts they are able to produce have difficulty adopting the correct conformation that imparts their special activity. These large amounts of protein begin to accumulate and congregate together forming insoluble particles within the cell that are called inclusion bodies. Often these proteins need to be unfolded into a linear amino acid sequence and then refolded to yield an active protein. Techniques for recovery from these complex biological soups require solid/liquid separations, filtrations, precipitations, chromatography, etc.

Some intracellular enzymes are used commercially without isolation and purification but the majority of commercial enzymes and therapeutic proteins are either produced extracellularly by the microbe and must be recovered from the liquid phase, or they are produced intracellularly by the microbe and must be recovered from the cells and further processed. For recovery of intracellular proteins at an industrial scale, solids/liquid separation is generally required for separation of cell mass, the removal of cell debris after cell breakage and the collection of precipitates. This can be done by filtration or centrifugation. In general, filtration is used to remove unwanted cells or cell debris whereas centrifugation is a preferred method for the collection of required solid material.

Various methods for recovery and/or purification of proteins are described in the literature. These methods include cell disruption, microfiltration, ultrafiltration, various forms of chromatography and ion exchange, as well as aqueous two-phase extraction (also called aqueous biphasic partitioning) using water-soluble polymers (including polyglycols and nonionic surfactants). See, for example, M. P. Deutscher, Ed., "Guide to Protein Purification," Methods in Enzymology," Vol. 182, Academic Press, San Diego, (1990); H. B. Blanch and D. S. Clark, "Biochemical Engineering," Marcel Dekker, New York, 1997, pp. 474-482; P. A. Belter, E. L. Cussler and W. Hu, "Bioseparations: Downstream Processing for Biotechnology," Wiley, New York, 1988, Chapter 5, 55. 99-143; and M. R. Ladisch, "Bioseparation Engineering," Wiley Interscience, New York, 2001.

Aqueous two-phase extraction has been widely used for the separation and concentration of proteins and nucleic acids. The two-phase aqueous systems are generally made up of (i) two immiscible polymer components, both water-soluble, such as polyethylene glycol and dextran; or (i) a single polymer component, such as polyethylene glycol, and aqueous salt solution; or (iii) water-miscible organic solvent, such as ethanol, and aqueous salt solution; or (iv) a non-ionic detergent and hydrophilic polymers, such as polyethylene glycol and dextran. See, for example, A. Louwrier, "Model Phase Separations of Proteins Using Aqueous/Ethanol Components", Biotechnology Techniques, Vol. 12, No. 6, pp. 363-365 (1998); A. Louwrier, "Model Isolations of Nucleic Acids from Prokaryotic Sources Using an Inorganic/Aqueous Biphasic System", Biotechnology Techniques, 13, pp 329-330 (1999); A. Louwrier, "Nucleic Acid Removal from Taq Polymerase Preparations Using an Aqueous/Organic Biphasic System", Biotechnology Techniques, 27, pp 444-445 (1999); Ulf Sivars et al, "Mechanism of Phase Behavior and Protein Partitioning in Detergent/Polymer Aqueous Two-Phase Systems for Purification of Integral Membrane Proteins", Biochemica and Biophysica Acta, 1474, pp 133-146 (2000); and Jorge Lorwin et al, "Oxidative Renaturation of Hen Egg-White Lysosyme in Polyethylene-Salt Aqueous Two-Phase Systems", Biotechnology and Bioengineering, Vol. 65, No. 4, pp. 437-446 (1999).

British Patent No. 2,333,526A discloses a process for extracting a nucleic acid from biochemical material using a biphasic system made of (i) a water miscible organic solvent which is preferably short chain alcohol such as methanol; and (ii) water, in combination with a partitioning agent. The two solvents, the water miscible organic solvent and water, are normally 100 percent miscible. When a partitioning agent, which is preferably an inorganic salt such as a phosphate, sulphate or carbonate, is added to the water component a biphasic system is formed. The aqueous phase contains nucleic acid and the organic phase contains the majority of proteins. The organic and aqueous phases are then separated by decantation or centrifugation.

International Patent Publication No. WO 00/12537 discloses a process for the preparation of biologically active somatotropin from inclusion bodies of a recombinant host cell containing an inactive form of the somatotropin protein involving the steps of: (a) contacting the inclusion bodies with an aqueous alcohol solution, particularly an aqueous n-propyl or isopropyl alcohol, at an alkaline pH to solubilize the protein; and (b) bringing the solubilized protein into contact with a mild oxidising agent to refold and form intramolecular disulfide bond between cysteine residues of the protein.

Hans-Olof Johansson et al., "Thermoseparating Water/Polymer System: A Novel One-Polymer Aqueous Two-Phase System for Protein Purification", *Biotechnology and Bioengineering*, Vol. 66. No. 4, pp. 247-257 (1999), describes the partitioning and separation of proteins using an aqueous two-phase system composed of only one polymer in water solution. The polymer is a linear random copolymer composed of ethylene oxide and propylene oxide groups which has been hydrophobically modified with myristyl groups at both ends. The polymer thermoseparates in water with cloud point at 14° C.

The known processes for the extraction/purification of intracellular proteins are not efficient and require disruption of cellular walls, folding and refolding of the proteins. Because the cell wall must be disrupted, the contents of the cell are released and mixed with the desired protein. The isolation of the active protein from this soup of impurities is difficult and expensive due to the requirement for numerous processing steps needed to deal with the variety and quantity of impurities. Thus, there exists a need for a more effective and efficient method for extraction of intracellular proteins. An improved method for the extraction of a protein from a fermentation broth that does not disrupt cell walls and does not require folding and refolding of enzymes has now been discovered. This new method uses certain oxygenated organic solvents that are water miscible or partially water miscible.

The invention involves the use of water miscible alcohols, water miscible glycol ethers, or partially water miscible glycol ethers to extract intracellular protein from whole fermentation broth. In the context of the present invention, the term whole fermentation broth means broth that has not been filtered to remove the biomass including cells. Water miscible alcohols and water miscible glycol ethers are completely miscible with water in all proportions in the temperature range from 20° C. to 80° C. All other alcohols are partially water miscible alcohols and all other glycol ethers are partially water miscible glycol ethers.

In one aspect, the present invention concerns a method for extracting an intracellular protein from a fermentation broth comprising the steps of:
(a) intermixing a sufficient quantity of a water miscible alcohol or glycol ether with an aqueous fermentation broth at a temperature at which a single phase comprising a protein, the water miscible alcohol or glycol ether, and water is formed;
(b) separating the phase comprising the protein, the water miscible alcohol or glycol ether, and water formed in step (a) from solid biomass impurities; and, optionally,
(c) recovering the protein from the phase obtained in step (b) by any conventional protein recovery method.

In another aspect, the present invention concerns a method for extracting an intracellular protein from a fermentation broth comprising the steps of:

(a) intermixing a sufficient quantity of a partially water miscible glycol ether with an aqueous fermentation broth at a temperature such that two phases are formed, a first phase comprising a protein, partially water miscible glycol ether, and water; and a second phase comprised mainly of partially miscible glycol ether;
(b) separating the second phase formed in step (a) from the first phase,
(c) separating the first phase obtained in step (b) from solid biomass impurities; and, optionally,
(d) recovering the protein from the first phase obtained in step (c) by any conventional protein recovery method.

In still another aspect, the present invention concerns a method for extracting an intracellular protein from a fermentation broth comprising the steps of:
(a) intermixing a sufficient quantity of a partially water miscible glycol ether with an aqueous fermentation broth at a temperature such that two phases are formed, a first phase comprised mainly of a partially water miscible glycol ether, and water; and a second phase comprising a protein and partially miscible glycol ether;
(b) separating the second phase formed in step (a) from the first phase,
(c) separating the second phase obtained in step (b) from solid biomass impurities; and, optionally,
(d) recovering the protein from the second phase obtained in step (c) by any conventional protein recovery method.

The method of the present invention is useful for the extraction of proteins from an aqueous fermentation broth. As used herein, the terms "protein" and "proteins" shall be construed to include all polymers of amino acid residues of any length, and thus the term includes polypeptides, as well as conventionally termed proteins which are a subset of polypeptides, and also peptides, which are the shorter, building block polymers which are made from alpha amino acids joined by amide bonds. Proteins generally include any sequence of amino acids for which the primary and secondary structure of the sequence is sufficient to produce higher levels of tertiary and/or quaternary structure. Proteins are distinct from peptides in that peptides lack the capability to form such tertiary and/or quaternary structure. Proteins typically have a molecular weight of at least about 15 kilodaltons. In the context of this specification, it will be appreciated that the amino acids may be the L-optical isomer or the D-optical isomer and may include synthetic amino acids.

The method of the present invention is particularly useful for the extraction of proteins expressed as inclusion bodies within the cell of the organism. In the context of the present invention, the term "inclusion bodies" refers to cytoplasmic aggregates containing heterologous proteins expressed in a transformed host cell, which can be recovered by separating from the cytoplasm.

For example, the present invention is suitable for, but not limited to, the extraction of an amylase enzyme from a whole fermentation broth. Amylases are one of the most commonly used classes of industrial enzymes. Amylases find applications in starch processing, baking, brewing, alcohol production, textile and other industries.

In this example, α-amylase enzyme is extracted from the fermentation broth in a single liquid phase using an aqueous solution comprising water and an alcohol, water miscible glycol ether or a partially water miscible glycol ether without disrupting cells integrity and without pretreatment steps specifically designed to lyse the cells. The extracted enzyme maintains most of its activity.

Non-limiting examples of alcohols that are useful in the practice of the present invention are methanol, ethanol, 2-propanol (IPA), and 2-methyl-2-propanol. The alcohol 2-propanol is a preferred alcohol.

A mixture of two or more alcohols can also be used in the method of the present invention to tailor the solvent for a specific protein and optimize performance.

Glycol ethers that are useful in the practice of the present invention are water miscible or partially water miscible. The glycol ethers exhibit both hydrophobic and hydrophilic characteristics because of the presence of hydrophobic alkyl groups and hydrophilic oxygen-containing functional groups (hydroxyl groups and ether linkages). Some of glycol ethers also exhibit relatively low aquatic and mammalian toxicity compared with other organic solvents.

Many glycol ethers exhibit inverse solubility in water such that the solubility in water at 100° C. is at least 1 weight percent less than the solubility in water at −5° C. This inverse solubility behavior can be attributed to temperature-sensitive hydrogen bonding. It is known that many glycol ethers exhibit a lower critical solution temperature (LCST), below which they are completely miscible with water. At temperatures below the LCST, the glycol ether is able to form hydrogen bonds with water and this attractive interaction leads to complete miscibility. At temperatures above the LCST, hydrogen bonding is disrupted by increasing thermal energy and hydrophobic interactions between the glycol ether and water begin to dominate. This results in partial miscibility and a decrease in the solubility of the glycol ether in water with increasing temperature (termed inverse solubility). Depending on the particular glycol ether, the LCST can be as low as −10° C. or as high as 100° C. The glycol ethers, both water soluble and partially water soluble are well known in the art and various methods for their preparation are described in the literature and practiced commercially.

Non-limiting examples of water miscible glycol ethers that are useful in the practice of the present invention and are completely miscible with water in the temperature range of from about 20° C. to about 80° C. include ethylene glycol n-propyl ether (EP), propylene glycol ethyl ether (PE), propylene glycol methyl ether (PM), diethylene glycol n-butyl ether (DB), diethylene glycol ethyl ether (DE), diethylene glycol methyl ether (DM), triethylene glycol n-butyl ether (TB), triethylene glycol n-pentyl ether (TPent), triethylene glycol ethyl ether (TE), triethylene glycol methyl ether (TM), and diethylene glycol dimethyl ether (DGDME).

Non-limiting examples of partially water miscible glycol ethers that are useful in the practice of the present invention and are miscible with water at the temperature of about 20° C. but become only partially miscible with water as the water-ethylene glycol solution is heated include ethylene glycol n-butyl ether (EB), ethylene glycol iso-butyl ether (EiB), propylene glycol n-propyl ether (PnP), dipropylene glycol ethyl ether (DPE), dipropylene glycol iso-propyl ether (DPiP), Diethylene glycol 2-methylbutyl ether (D2 MB), diethylene glycol n-pentyl ether (DPent), triethylene glycol n-heptyl ether (THept), triethylene glycol n-hexyl ether (THex), diethylene glycol ethyl ether acetate (DEA), and diethylene glycol diethyl ether (DGDEE).

Non-limiting examples of partially water miscible glycol ethers that are useful in the practice of the present invention that form a separate phase with water at about 20° C. and separate further upon heating include ethylene glycol 2-methylbutyl ether (E2 MB), ethylene glycol n-hexyl ether (EHex), ethylene glycol n-pentyl ether (EPent), propylene glycol n-butyl ether (PnB), propylene glycol tert-butyl ether (PtB), propylene glycol iso-propyl ether (PiP), dipropylene glycol n-butyl ether (DPnB), dipropylene glycol n-propyl ether (DPnP), diethylene glycol n-hexyl ether (DHex), tripropylene glycol n-butyl ether (TPnB), tripropylene glycol n-propyl ether (TPnP), ethylene glycol ethyl ether acetate (EEA), ethylene glycol n-butyl ether acetate (EBA), diethylene glycol n-butyl ether acetate (DBA), propylene glycol methyl ether acetate (PMA), ethylene glycol diethyl ether (EGDEE), ethylene glycol dibutyl ether (EGDBE), diethylene glycol dibutyl ether (DGDBE), and dipropylene glycol dimethyl ether (DMM).

A mixture of two or more glycol ethers can also be used in the method of the present invention to tailor the solvent for a specific protein and optimize performance.

According to the present invention, a protein is extracted from a whole aqueous fermentation broth using an alcohol, water miscible glycol ether or a partially water miscible glycol ether. The exact nature of the action of the alcohol, water miscible glycol ether or partially water miscible glycol ether in the method of the present invention is not known, but it is believed that the invention facilitates movement of the protein present in the biomass solids through the cell wall into an aqueous solution on addition of the alcohol, water miscible glycol ether or partially water miscible glycol ether. The cell wall remains intact and the majority of alpha-amylase enzyme activity is retained.

It is important to note that in some embodiments the protein may be extracted such that it is solubilized predominantly in the water, while in other embodiments the protein is solubilized predominantly in the alcohol or glycol ether. This partitioning, which may in some cases be a function of the nature of the protein itself and in others of the relative proportions of the alcohol or glycol ether and the water, or both, may facilitate ultimate recovery of the protein by first separating the alcohol or glycol ether from the water by forming two distinct phases. For example, certain proteins tend to be more lipophilic or hydrophobic, and may in that case tend to partition predominantly into the glycol ether portion, while other proteins tend to be more lipophobic or hydrophilic and may therefore tend to partition predominantly into the water portion. In some cases a protein may not tend to partition at all, but is rather extracted in comparable amounts into each component, suggesting employment of recovery means other than those involving such separation of the glycol ether and water by forming two distinct phases. Those skilled in the art will understand that, via modeling and/or routine experimentation, the likely destination of the protein upon its extraction may be easily determined.

In certain cases, it is advantageous to heat the fermentation broth followed by the addition of a small amount of ethylene-diamine-tetraacetic acid (EDTA) or another chelating compound prior to the extraction of a protein to remove metal ions from the cell walls to increase the permeability of the cell walls.

Conveniently, the method of the present invention is conducted at a temperature of from about 1° C. to about 100° C., preferably from about 20° C. to about 40° C.

The biomass impurities present in the aqueous protein solution can be removed via any known method such as, for example, via centrifugation or microfiltration. High speed batch centrifugation can be used for removal of biomass impurities.

When a partially water miscible glycol ether is used in the process of the present invention and this results in formation of an organic phase comprised mainly of the partially water miscible glycol ether, the glycol ether can be recovered from the liquid organic phase and recycled into the method. The recovery and recycling of the glycol ether should be achieved with little loss of the glycol ether in order to achieve good method economics. Methods that can be used to recover the partially water miscible glycol ether from the organic phase include distillation, evaporation, and chromatography. Distillation is a preferred method.

Also, if desired, the alcohol and water miscible glycol ether can be recovered from the single aqueous phase comprising the protein, alcohol or glycol ether, as can the glycol ether dissolved in the aqueous phase when a partially miscible glycol ether is used. Distillation is a preferred method for recovery of the alcohol. The recovery of dissolved partially water miscible glycol ether can be facilitated by heating the aqueous solution to reduce the saturation amount of glycol ether present in the aqueous phase. Recovery partially water miscible glycol ether from the aqueous phase may be accomplished by steam stripping provided that the partially water miscible glycol ether is sufficiently volatile or hydrophobic. In addition, water miscible or partially water miscible glycol ethers may be recovered from aqueous solutions via liquid-liquid extraction using hydrophobic organic solvents such as 2-ethyl hexanol.

If desired, the protein product can be concentrated by any known concentration method such as, for example, by extraction of water into a water-lean glycol ether (that is, one that is not saturated with water), or by evaporation such as in a wiped-film evaporator.

The temperature at which the intermixing of the organic oxygenated solvent with the aqueous fermentation broth in step (a) of the method of the present invention is not critical and can conveniently be from about 1° C. to about 90° C., preferably from about 20° C. to about 40° C. The temperature used is dependent upon the particular glycol ether used and the particular protein.

The method of the present invention is advantageously carried out at atmospheric pressure, although higher and lower pressures may be used in certain cases.

A person skilled in the art may readily select the amount of an alcohol or glycol ether which may be used. Generally speaking, a sufficient amount of the alcohol or glycol ether must be used to obtain substantial recovery of the desired protein from the aqueous fermentation broth. This can be readily determined by experimentation.

The method of the present invention can be carried out in a batch operation or continuously, and may be conducted in any conventional extraction equipment.

The present invention's method may be carried out at a variety of pH levels. For example, in one embodiment a pH from about 4 to about 11 may be used. In other embodiments, a pH from about 5 to about 9 may be employed, and in still other embodiments a pH from about 6 to about 8 may be used. Those skilled in the art will be easily familiar with ways and means to ensure a desired pH level, and will understand that pH extremes may, in some embodiments, result in undesirable cell and/or protein degradation.

If desired, additional equipment can be used in the method of the present invention such as additional extraction, distillation or evaporation equipment for recovery of dissolved glycol ether from the aqueous phase and the organic phase, and for recovery and recycle of the hydrophobic co-solvent, when used. Such additional equipment and its use in liquid-liquid extraction methods are well known in the art. A person of an ordinary skill in the art would use such additional equipment or combination thereof in the method of the present invention in a manner known for use of such equipment in conventional liquid-liquid extraction methods. The use of such additional equipment or combination thereof will depend on many factors, such as, for example, the nature of the protein, the nature of other compounds present in the fermentation broth, the nature of the glycol ether used, the use of the hydrophobic organic solvent, the costs associated with the use of glycol ether and/or hydrophobic solvent, the costs associated with the use of additional equipment, and the overall economics of the entire process.

EXAMPLES

The invention is demonstrated by the example of one embodiment involving extraction of alpha-amylase enzyme from whole fermentation broth. The enzyme activity after extraction by the method of the present invention is determined by one of two different calorimetric methods. The first method is modeled after procedures given in experiments 10.1 and 10.8 described in David T. Plummer's book, *An Introduction to Practical Biochemistry*, McGraw-Hill, New York, 1971, where a salivary alpha-amylase enzyme is used instead. This method detects the sugar maltose produced when the alpha-amylase enzyme is used to hydrolyze the alpha-1→4 links of a starch sample. A spectrophotometer is used to measure the absorbance of the resulting maltose solution at 540 nm. The second method relies on the detection of 4-nitrophenol liberated when the alpha-amylase enzyme is used to hydrolyze a sample of 4-nitrophenyl-alpha-D-hexa-(1→4)-glucopyranoside substrate. A spectrophotometer is used to measure the absorbance of the resulting 4-nitrophenol solution at 405 nm.

All parts, percentages and ratios herein are by weight unless otherwise indicated.

The invention will be further clarified by a consideration of the following examples which are intended to be purely exemplary of the present invention.

General Test Procedures

Enzyme Activity: The enzyme activity was determined using one of two tests.

In the first test, the activity of the enzyme was assessed using a qualitative Yes/No test. The test was performed on the extracted liquid after extraction using a starch hydrolysis method with calorimetric detection of the product sugar. The starch substrate was converted to maltose which was then detected using a spectrophotometer to measure UV absorbance. The test procedure is modeled after procedures given in experiments 10.1 and 10.8 of David T. Plummer's book, *An Introduction to Practical Biochemistry*, McGraw-Hill, New York, 1971, where a salivary alpha-amylase enzyme is used instead.

*Preparation of Test Reagents.* A phosphate buffer (0.1 M, pH 6.86) was prepared using a commercially available, ready-to-dilute, phosphate buffer salt concentrate, and a 1 percent NaCl solution was prepared by dissolving the appropriate amount of NaCl in water. A buffered starch substrate was made using the prepared phosphate buffer (0.5 percent starch in phosphate buffer). Soluble starch (5 g) and a stir bar were placed in a tared beaker which was then placed on a stirring plate. Phosphate buffer (50 mL) was added, and the resulting mixture stirred until a smooth paste was obtained. The paste was added to 500 mL of boiling phosphate buffer and allowed to boil for about one minute. The solution was then cooled to room temperature and diluted to 1 L with the phosphate buffer. A dinitrosalycilate reagent required for the test was prepared as follows: Sodium potassium tartrate (150 g) was dissolved in water (250 mL) in a volumetric flask. The 3,5-dinitrosalicylic acid was placed in a tared beaker along with 2N sodium hydroxide (100 mL) and a magnetic stir bar. The beaker was then placed on a stirred hot-plate and the mixture heated to about 60° C. The mixture was allowed time to heat and stir until a solution formed. While still hot, the contents of the beaker were placed in a 500-mL volumetric flask that already contained the sodium potassium tartrate solution. The reagent mixture was then diluted to 500 mL.

Test Procedure. Tests were conducted in a series of 50 mL vials, one of which was labeled as the blank. To each of the vials was added 0.5 percent starch solution (12.5 mL), 0.1 M phosphate buffer (5 mL), and 1 percent NaCl solution (2.5 mL). Water (2.5 mL) was added to the vial labeled as the blank. A sample of a given aqueous or solvent test solution (2.5 mL) was added to another vial which was then labeled appropriately. This last step was repeated with the remaining test samples, each time using a different vial. The vials were capped and placed in a 37° C. water bath for 20 minutes. The vials were removed from the bath and the enzymatic reaction quenched by the addition of 2N NaOH (2.5 mL) to all of the vials. The dinitrosalicylate reagent (2.5 mL) was added to each of the vials which were then capped and heated for exactly 5 minutes in a boiling water bath. The vials were allowed to cool to room temperature before transferring the contents to cuvettes. A Hach DR/2010 Spectrophotometer was used to measure the absorbance of each solution at a wavelength of 540 nm. The blank was used to zero the instrument. The test was interpreted to indicate a reduction of activity if the measured absorbance value was lower than the absorbance value measured for a starch sample treated with a stock solution of alpha-amylase. The activity was considered to be fully retained if the absorbance value was the same or higher. The results were reduced to Yes (activity was retained) and No (a significant reduction of activity had occurred). The results obtained are summarized in Tables 2 and 5.

Specific enzyme activity was assessed by measuring the p-nitrophenol liberated by reaction of the enzyme with p-nitrophenyl-α-D-hexa-(1→4)-glucopyranoside (p-NP substrate).

Preparation of Reagents. A 0.05 M MOPS buffer was prepared by dissolving 11.55 g MOPS (3-(N-morpholino) propanesulfonic acid, sodium salt) in 1 L Milli-Q-water (from Millipore Water System) and adjusting the pH to 7 with 1 N HCl. A 6 M urea solution was prepared by dissolving 72 g urea in 200 mL Milli-Q-water. A 5 mM p-NP substrate solution was prepared by weighing 111-222 mg p-NP into a tared 50-mL plastic centrifuge tube and diluting with 0.05 M MOPS buffer. A standard 10 mM 4-nitrophenol solution was prepared by weighing 140 mg into a tared 100-mL volumetric flask and diluting to volume with 0.05 M MOPS buffer. The pH of the 4-nitrophenol solution was adjusted to 7 with either 1 N HCl or 1 N NaOH. A 1 mM 4-nitrophenol calibration standard was prepared by diluting the 10 mM solution with 0.05 M MOPS buffer. Alpha-amylase samples and standard solutions were thoroughly stirred prior to sampling. About 1.0±0.1 g alpha-amylase sample or stock solution was weighed in a 5-dram vial and then diluted with 9.0 mL 6 M urea solution. A 1.0 mL aliquot of the resulting urea-enzyme solution was then transferred to a 5-dram vial and diluted with 9.0 mL of the 0.05 MOPS solution.

Test Procedure. Exactly 950 microliters of the 0.05 M MOPS buffer was transferred to a microcuvette and the cuvette placed into a water-heated cuvette heating block at 75° C. for several minutes. The cuvette was then removed from the heating block, water wiped off, and placed into the constant temperature reference compartment (75° C.) of a Shimadzu UV-161 spectrophotometer. This operation was repeated with another cuvette which was placed in the sample compartment of the spectrophotometer. The absorbance of the cuvette+MOPS buffer was nulled by zeroing the spectrophotometer. Exactly 50 microliters of the 1 mM 4-nitrophenol standard was transferred into the sample cuvette with a micropipette. The solutions were mixed well by gently pipetting up and down several times the liquid in the cuvette, and then by sealing the cuvette and inverting it two times. The absorbance of the solution was then measured three times at 405 nm. Exactly 950 microliters of the 5 mM p-NP substrate solution was transferred to a microcuvette and the cuvette placed into a water-heated cuvette heating block at 75° C. for several minutes. The cuvette was removed from the heating block, water wiped off, and placed into the constant temperature sample compartment (75° C.) of the spectrophotometer. After several minutes, 50 microliters of the dilute enzyme solution prepared earlier was added to the cuvette. The solutions were mixed well as described before for the 4-nitrophenol reference standards, and then the absorbance of the solution was measured at 405 nm. Enzyme activity concentrations were obtained by comparing the absorbance readings with those obtained with the 1 mM p-nitrophenol calibrating standard taking into account dilution factors. The results obtained are summarized in Table 6.

Enzyme concentrations were also established by high pressure liquid chromatography (HPLC) using an Agilent 1100 Series Liquid Chromatograph equipped with an ultraviolet (UV) detector set at 280 nm, and a Dell Ultra Scan P1110 ChemStation. The instrument was fitted with a PLRP-S 5 micron, 100A, 250×4.6 mm reversed phase column from Polymer Labs. The mobile phase was composed of (A) 0.025 M ammonium acetate (adjusted to pH 9 with NH$_4$OH) and 10 percent acetonitrile; and (B) 0.025 M ammonium acetate (adjusted to pH 9 with NH$_4$OH) and 70 percent acetonitrile. The analysis used a flow rate of 1 mL/min and a gradient of 100 percent (A) to 35 percent (A) in 40 minutes with a 3 minute hold. Injection size was 25 microliters. Samples were prepared by diluting 1.00 g of the aqueous or solvent test solution with 10.00 g HPLC grade water. Calibration standards contained between 10 and 1000 ppm alpha-amylase.

When needed, water and solvent concentrations were established by capillary gas chromatography. A Hewlett-Packard 6890 gas chromatograph equipped with capillary inlets, thermal conductivity detectors (TCD), HP-7683 auto-injectors, and a Chemstation was used for these analyses. Samples and calibration standards were diluted 5:1 with tetrahydrofuran (THF), which was used as the diluent, internal standard, and reference solvent. Calibrations were made using a 50 weight percent solvent in water solution after establishing the linearity range for the analyses. Data were recorded as the average of multiple injections.

Examples 1 to 11 and Comparative Examples C-1 and C-2

Single-Liquid System:

The whole fermentation broth containing α-amylase BD5088 (a heat stable, low pH enzyme with a molecular weight of ~49 kDaltons (kDa) and an isoelectric point (pI) of 4.5), obtained by fermentation of the production organism *Pseudomonas fluorescens*, was heat treated for 30 minutes at 70° C. An organic solvent that is miscible in water was added to the fermentation broth. After agitation of the mixture for about 30 minutes, only one liquid phase is present. In most cases, biomass solids were separated from the resulting liquid using a high-speed batch centrifuge. The results are shown in Table 1 that follows. A number of the examples listed in Tables 1 to 3 are duplicate experiments that were carried out to better understand experimental variability. Although the results show some variability, the trends in the data are consistent.

Two types of examples were performed. One set of examples involved adding 15 g of the solvent to 15 g of the fermentation broth. These examples are indicated in Table 1 by the solvent to fermentation broth ratio of 1.0. The other set of examples involved first diluting 7.5 mL of the fermentation broth with 7.5 mL of water and then adding 15 mL of the solvent. This resulted in a significantly higher ratio of extraction liquid to the fermentation broth, although the concentration of the solvent in the liquid after extraction was not greatly different. These examples are indicated in Table 1 by the solvent to fermentation broth ratio between 2.6. In this case, this ratio is defined as the ratio of the weight of added liquid, including water and solvent to the weight of the initial feed broth, prior to extraction.

TABLE 1

Results of Whole Broth Extractions Involving a Single Liquid Phase

| Example | Solvent System | Temp (° C.) | Solvent to Feed Ratio Weight of Added Liquid to Weight of Feed Broth prior to Extraction (wt/wt) | Concentration of Enzyme in the Liquid after Extraction (ppm-wt) | Recovery of Enzyme from the Feed Broth into the Liquid after Extraction (%) |
|---|---|---|---|---|---|
| C-1* | Water alone | 22 | 1.0** | 95 | 3 |
| C-2* | Water alone | 50 | 1.0** | 178 | 6 |
| 1 | IPA-water | 22 | 1.0** | 237 | 7 |
| 2 | IPA-water | 22 | 1.0** | 199 | 6 |
| 3 | IPA-water | 22 | 1.0** | 350 | 11 |
| 4 | IPA-water | 22 | 2.6*** | 638 | 35 |
| 5 | EB-water | 22 | 1.0** | 908 | 27 |
| 6 | EB-water | 22 | 1.0** | 1900 | 57 |
| 7 | PM-water | 22 | 1.0** | 2920 | 88 |
| 8 | PM-water | 22 | 1.0** | 2850 | 86 |
| 9 | PM-water | 22 | 1.0** | 2690 | 81 |
| 10 | PM-water | 22 | 1.0** | 2780 | 84 |
| 11 | PM-water | 50 | 1.0** | 3300 | 99 |

*not an example of the present invention.
**equal weights of whole broth and solvent were mixed.
***diluted 7.5 mL broth with 7.5 mL of water, then added 15 mL of solvent.

The concentration of enzyme in the feed broth was approximately 6380 ppm. The concentration of biomass was 8.7 weight percent.

In all of the examples in Table 1, broth that had been stored frozen for several months was used.

The liquid-phase enzyme concentrations determined by high pressure liquid chromatography (HPLC) analysis were used to calculate the amount of enzyme recovered from the biomass solids into the liquid phase. Since the enzyme is expressed as inclusion bodies within the cell, it is originally associated with the biomass. The data in Table 1 show that a significant fraction of the α-amylase present as inclusion bodies within the cells are efficiently extracted out of a heat treated whole fermentation broth into a single liquid phase containing roughly equal amounts of water and glycol ether without pretreatment steps specifically designed to lyse the cells.

The results of Yes/No enzyme activity tests performed on the extracted liquid are shown in Table 2 that follows.

TABLE 2

Yes/No Activity Test Results for Examples Shown in Table 1

| Ex. | Solvent System | Temp (° C.) | Measured Enzyme Concentration in the Extract Liquor | Concentration of Enzyme in the Activity Test Sample after Sample Preparation (ppm) | Measured Absorbance | Absorbance Expected for that Enzyme Concentration Assuming No Loss of Bioactivity | Activity Retained (Yes/No) |
|---|---|---|---|---|---|---|---|
| 1 | IPA-water | 22 | 237 | 0.4 | 3.3 | 1.5+ | Yes |
| 5 | EB-water | 22 | 908 | 1.3 | 3.02 | 2.9+ | Yes |
| C-1 | Water alone | 22 | 95 | 0.16 | 3.53 | 0.5+ | Yes |
| C-2 | Water alone | 50 | 178 | 0.28 | 2.37 | 1.0+ | Yes |

Examples 12 to 19

Two-Liquid System

Equal weights of glycol ether and a whole fermentation broth were mixed at a temperature that allowed formation of two phases, that is, an aqueous liquid phase and an organic liquid phase rich in the glycol ether. The α-amylase enzyme recovery was increased roughly to 50 percent for EB (at 60° C.), and 70 percent for PnP (at 22° C.). Although the organic phase contained up to 33 percent dissolved water by weight, less than 10 parts per million (ppm) of enzyme was detected in the organic phase. Essentially all of extracted α-amylase enzyme was present in the liquid aqueous phase. The results obtained are given in Tables 3 and 4 that follow. A number of the examples given in Tables 3 and 4 are duplicate experiments that were carried out to better understand experimental variability. Although the results show some variability, the trends in the data are consistent.

TABLE 3

Results of Whole Broth Extractions Involving Two Liquid Phases

| Example | Solvent System | Temp (° C.) | Weight of Added Solvent to Weight of Feed Broth prior to Extraction (wt/wt) | Concentration of Enzyme in the Aqueous Phase after Extraction** (ppm-wt) | Concentration of Glycol Ether in the Aqueous Phase (wt %) | Concentration of Water in the Organic Phase (wt %) |
|---|---|---|---|---|---|---|
| 12 | PnP-water | 22 | 1.0 | 5350 | 22 | 33 |
| 13 | PnP-water | 22 | 1.0 | 5180 | 22 | 33 |
| 14 | EB-water | 60 | 1.0 | 3060 | 17 | 31 |
| 15 | EB-water | 60 | 1.0 | 3750 | 17 | 31 |
| 16 | PnB-water | 50 | 1.0 | 250 | 4.9 | 12.8 |
| 17 | PnB-water | 22 | 1.0 | 190 | 5.6 | 13.3 |
| 18 | PnB-water | 22 | 1.0 | 160 | 5.6 | 13.3 |
| 19 | PnB-water | −5 | 1.0 | 177 | 5.0 | 15.4 |

TABLE 4

Results of Whole Broth Extractions Involving Two Liquid Phases

| Example | Solvent System | Temp (° C.) | Weight of Feed Broth | Approx. Weight of Aqueous Phase after Extraction* (grams) | Approx. Weight of Organic Phase after Extraction* (grams) | Recovery of Enzyme from the Feed Broth into the Aqueous Phase after Extraction** (%) |
|---|---|---|---|---|---|---|
| 12 | PnP-water | 22 | 15 | 13 | 17 | 70 |
| 13 | PnP-water | 22 | 15 | 13 | 17 | 70 |
| 14 | EB-water | 60 | 15 | 13 | 17 | 40 |
| 15 | EB-water | 60 | 15 | 13 | 17 | 50 |
| 16 | PnB-water | 50 | 10 | 9 | 11 | 4 |
| 17 | PnB-water | 22 | 10 | 9 | 11 | 3 |
| 18 | PnB-water | 22 | 10 | 9 | 11 | 2 |
| 19 | PnB-water | −5 | 10 | 9 | 11 | 3 |

*determined from material balance
**less than 10 ppm enzyme was detected in the organic phase after extraction The concentration of enzyme in the feed broth was approximately 6380 ppm. The concentration of biomass was 8.7 weight percent.

The results of Yes/No enzyme activity tests performed on the extracted liquid are shown in Table 5 that follows.

TABLE 5

Yes/No Activity Test Results for Examples given in Tables 3 and 4

| Sample | Solvent System | Temp (° C.) | Measured Enzyme Concentration in the Extract Liquor | Concentration of Enzyme in the Activity Test Sample after Sample Preparation | Measured Absorbance | Absorbance Expected for that Enzyme Concentration Assuming no Loss of Bioactivity | Activity Retained Yes/No |
|---|---|---|---|---|---|---|---|
| 15 | EB-water Aqueous Layer | 60 | 3750 | 197 | 3.0 | 3.7+ | Yes, although some loss of activity is apparent |
|  | Organic Layer | 60 | 14 | 0.7 | 2.5 | 1.5+ | Some activity is detected even though only traces of enzyme were present in the sample |
| 13 | PnP-water Aqueous Layer | 22 | 5180 | No data* | — | — | No data* |
|  | Organic Layer | 22 | 15 | 0.8 | 0.2 | 1.5+ | Little activity |

*the aqueous phase was too small to test activity

The results of enzyme activity tests performed on the extracted liquid using a test utilizing p-nitrophenyl-α-D-hexa-glucopyranoside are shown in Table 6 that follows.

TABLE 6 p-Nitrophenyl-α-D-hexa-glucopyranaside Activity Test Results for Examples given in Tables 1, 3 and 4

| Solvent | Experiment No. | Temp (° C.) | Concentration of Enzyme in Extract Liquor (aqueous phase) | | Activity Retained (%) |
|---|---|---|---|---|---|
|  |  |  | LC (ppm) | Activity Assay (ppm) |  |
| 11 | PM | 50 | 3300 | 2900 | 88 |
| 10 | PM | 22 | 2800 | 2800 | 100 |
| 12 | PnP | 22 | 5370 | 4570 | 85 |
| 6 | EB | 22 | 1900 | 1040 | 55 |
| 14 | EB | 60 | 3060 | 2470 | 80 |
| 3 | IPA | 22 | 350 | 300 | 86 |
| 16 | PnB | 50 | 250 | 255 | 100 |
| 18 | PnB | 22 | 160 | 155 | 97 |

Experiments were carried out to determine if enzyme already dissolved in water would transfer into a separate glycol ether phase. The solvents used in these experiments were ethylene glycol n-butyl ether (EB), propylene glycol n-propyl ether (PnP), dipropylene glycol n-propyl ether (DPnP), tripropylene glycol n-propyl ether (TPnP), and dipropylene glycol dimethyl ether (DMM). The enzyme feed solutions were prepared from a purified α-amylase enzyme. Equal weights of the aqueous enzyme feed and the added solvent were used to maximize the potential for transfer of the enzyme there. In certain cases, this required operating at temperatures slightly above the LCST. In the case of EB, it required operating at 70° C. In all of these examples, only trace amounts of the enzyme were observed to transfer from the aqueous phase into the glycol ether phase. This was true even when significant amounts of water were present in the glycol ether phase (up to about 52 weight percent). Adjusting the pH over the range of 4-7 using buffer solutions did not alter this behavior. Using a pH of 2 caused precipitation of the enzyme but did not result in transfer of significant amounts of the enzyme into the glycol ether phase. The results obtained are given in Table 7 that follows.

TABLE 7

Results of Extraction Experiments Using Purified Enzyme Solution

| | | Experimental Conditions | | | | | | | | | |
|---|---|---|---|---|---|---|---|---|---|---|---|
| | | Ppm Enzyme in Aq. | pH of | Sampling | Aqueous Layer (wt %) | | | Organic Layer (wt %) | | | Activity Test (Absorbance) |
| Ex. # | Glycol Ether | Feed (ppm) | Enzyme Soln. | Temp (° C.) | Glycol Ether | Water | Amylase | Glycol Ether | Water | Amylase | Aqueous Layer | Organic Layer |
|---|---|---|---|---|---|---|---|---|---|---|---|---|
| 1 | PnP | 345.3 | 4 | 38 | 26.26 | 73.68 | 675 | 59.78 | 40.22 | 0.0 | 3.55 | 3.35 |
| 2 | PnP | 329.4 | 4 | 34 | 29.5 | 70.43 | 723 | 57.16 | 42.84 | 0.0 | 3.44 | 1.87 |
| 3 | PnP | 334.2 | 2 | 32 | 23.09 | 76.91 | 0.0 | 62.47 | 37.53 | 10.4 | 0.28 | N/A* |
| 4 | DPnP | 335.7 | 7 | 25 | 15.96 | 84.00 | 374 | 78.5 | 21.50 | 0.0 | 3.63 | 0.43 |
| 5 | DPnP | 345.3 | 4 | 17 | 30.99 | 68.97 | 400 | 62.89 | 37.11 | 0.0 | 3.72 | 0.93 |
| 6 | DMM | 334.6 | 5 | 10 | 42.51 | 57.47 | 182 | 94.93 | 5.07 | 0.0 | 3.40 | 0.09 |
| 7 | DMM | 335.9 | 4 | 10 | 43.96 | 56.02 | 187 | 94.19 | 5.81 | 0.0 | 3.46 | 2.02 |
| 8 | TPnP | 334.6 | 5 | 10 | 25.91 | 74.06 | 306 | 77.95 | 22.05 | 0.0 | 3.32 | 0.70 |
| 9 | TPnP | 335.9 | 4 | 10 | 31.08 | 68.89 | 338 | 76.92 | 25.86 | 0.0 | 3.46 | 0.03 |
| 10 | EB | 235.4 | 4 | 70 | 15.57 | 84.4 | 262 | 48.86 | 51.13 | 11.8 | 3.36 | 1.64 |

*alpha-amylase precipitated out of solution at this pH

The activity test results given in Table 7 indicate full activity for all of the aqueous samples. These solutions contained the enzyme plus a considerable amount of dissolved solvent. Interestingly, significant activity was also measured for some of the organic samples, even though LC analysis of the organic layer did not detect the presence of the enzyme. These results provide another example of how even very small amounts of the enzyme (<1 ppm in the test solutions) can catalyze significant hydrolysis of starch in the test.

The data in Table 7 also show that the enzyme solution may be concentrated to some extent by extraction of water into a pre-dried glycol ether phase; that is, one that is unsaturated with water prior to its use in the extraction. For example, experiments 1 and 2 demonstrate that PnP can double the α-amylase concentration by extracting water from the aqueous layer and reducing the size of the aqueous layer in half. Experiments 4, 5, and 10 demonstrate that DPnP and EB also yield a concentration effect. The TPnP and DMM, on the other hand, showed little if any concentration effect because an equal amount of glycol ether (approximately) also transferred into the aqueous phase.

Because the enzyme is retained almost exclusively in the aqueous phase, transfer of water and organic impurities out of the aqueous phase into the glycol ether phase can provide an opportunity to purify and concentrate an aqueous enzyme solution.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

The invention claimed is:

1. A method for extracting an intracellular protein from a fermentation broth comprising the steps of:
   (a) intermixing a sufficient quantity of a glycol ether with an aqueous fermentation broth at a temperature to form a single aqueous phase comprising a protein, the glycol ether, and water is formed;
   (b) separating the single aqueous phase comprising the protein, the glycol ether, and water formed in step (a) from solid biomass impurities; and, optionally,
   (c) recovering the protein from the single aqueous phase obtained in step (b) by any conventional protein recovery method, wherein the glycol ether is ethylene glycol n-propyl ether, propylene glycol ethyl ether, propylene glycol methyl ether, diethylene glycol n-butyl ether, diethylene glycol ethyl ether, diethylene glycol methyl ether, triethylene glycol n-butyl ether, triethylene glycol n-pentyl ether, triethylene glycol ethyl ether, triethylene glycol methyl ether, diethylene glycol dimethyl ether, ethylene glycol n-butyl ether, ethylene glycol iso-butyl ether, propylene glycol n-propyl ether, dipropylene glycol ethyl ether, dipropylene glycol iso-propyl ether, diethylene glycol 2-methylbutyl ether, diethylene glycol n-pentyl ether, triethylene glycol n-heptyl ether, triethylene glycol n-hexyl ether, diethylene glycol ethyl ether acetate, or diethylene glycol diethyl ether.

2. The method of claim 1, wherein the glycol ether is miscible with water in the temperature range from about 20° C. to about 80° C.

3. The method of claim 1, wherein the glycol ether is miscible with water at the temperature of about 20° C. and partially miscible when the glycol ether and water mixture is heated above 20° C.

4. The method of claim 1, wherein step (c) comprises separation of the glycol ether from the water to form two phases, wherein the protein remains predominantly in the aqueous phase, followed by recovery of the protein therefrom.

5. The method of claim 1 wherein steps (a)-(c) are carried out at a pH from about 4 to about 11.

6. A method for extracting an intracellular protein from a fermentation broth comprising the steps of:
   (a) intermixing a sufficient quantity of a partially water miscible glycol ether with an aqueous fermentation broth at a temperature such that two phases are formed, a first aqueous phase comprising a protein, partially water miscible glycol ether, and water; and a second phase comprised mainly of partially miscible glycol ether;
   (b) separating the first aqueous phase formed in step (a) from the second phase,
   (c) separating the first aqueous phase obtained in step (b) from solid biomass impurities; and, optionally,
   (d) recovering the protein from the first aqueous phase obtained in step (c) by any conventional protein recovery method, wherein the glycol ether is ethylene glycol n-butyl ether, ethylene glycol iso-butyl ether, propylene glycol n-propyl ether, dipropylene glycol ethyl ether, dipropylene glycol iso-propyl ether, diethylene glycol 2-methylbutyl ether, diethylene glycol n-pentyl ether), triethylene glycol n-heptyl ether, triethylene glycol n-hexyl ether, diethylene glycol ethyl ether acetate, diethylene glycol diethyl ether, ethylene glycol 2-methylbutyl ether, ethylene glycol n-hexyl ether, ethylene glycol n-pentyl ether, propylene glycol n-butyl ether, propylene glycol tert-butyl ether, propylene glycol iso-propyl ether, dipropylene glycol n-butyl ether, dipropylene glycol n-propyl ether, diethylene glycol n-hexyl ether, tripropylene glycol n-butyl ether, tripropylene glycol n-propyl ether, ethylene glycol ethyl ether acetate, ethylene glycol n-butyl ether acetate, diethylene glycol n-butyl ether acetate, propylene glycol methyl ether acetate, ethylene glycol diethyl ether, ethylene glycol dibutyl ether, diethylene glycol dibutyl ether, or dipropylene glycol dimethyl ether.

7. The method of claim 6, wherein the glycol ether is miscible with water at the temperature of about 20° C. and partially miscible with water when the temperature is heated above 20° C.

8. The method of claim 6, wherein the glycol ether forms a separate phase with water at about 20° C. and separates further upon heating.

9. The method of claim 6, wherein steps (a)-(c) are carried out at a pH from about 4 to about 11.

10. A method for extracting an intracellular protein from a fermentation broth comprising the steps of:
   (a) intermixing a sufficient quantity of a partially water miscible glycol ether with an aqueous fermentation broth at a temperature such that two phases are formed, a first aqueous phase comprised mainly of a partially water miscible glycol ether, and water; and a second phase comprising a protein and partially miscible glycol ether;
   (b) separating the second phase formed in step (a) from the first aqueous phase,
   (c) separating the second phase obtained in step (b) from solid biomass impurities; and, optionally,
   (d) recovering the protein from the second phase obtained in step (c) by any conventional protein recovery method,
   wherein the glycol ether is ethylene glycol n-butyl ether, ethylene glycol iso-butyl ether, propylene glycol n-propyl ether, dipropylene glycol ethyl ether, dipropylene glycol iso-propyl ether, diethylene glycol 2-methylbutyl ether, diethylene glycol n-pentyl ether), triethylene glycol n-heptyl ether, triethylene glycol n-hexyl ether, diethylene glycol ethyl ether acetate, diethylene glycol diethyl ether, ethylene glycol 2-methylbutyl ether, ethylene glycol n-hexyl ether, ethylene glycol n-pentyl ether, propylene glycol n-butyl ether, propylene glycol tert-butyl ether, propylene glycol iso-propyl ether, dipropylene glycol n-butyl ether, dipropylene glycol n-propyl ether, diethylene glycol n-hexyl ether, tripropylene glycol n-butyl ether, tripropylene glycol n-propyl ether, ethylene glycol ethyl ether acetate, ethylene glycol n-butyl ether acetate, diethylene glycol n-butyl ether acetate, propylene glycol methyl ether acetate, ethylene glycol diethyl ether, ethylene glycol dibutyl ether, diethylene glycol dibutyl ether, or dipropylene glycol dimethyl ether.

11. The method of claim 10, wherein the glycol ether is miscible with water at the temperature of about 20° C. and partially miscible with water when the temperature is heated above 20° C.

12. The method of claim 10, wherein the glycol ether forms a separate phase with water at about 20° C. and separates further upon heating.

13. The method of claim 10, wherein steps (a)-(c) are carried out at a pH from about 4 to about 11.

\* \* \* \* \*